(12) United States Patent
Shimada et al.

(10) Patent No.: US 10,932,663 B2
(45) Date of Patent: Mar. 2, 2021

(54) PERIMETER

(71) Applicant: KOWA COMPANY, LTD., Aichi (JP)

(72) Inventors: Satoshi Shimada, Tokyo (JP); Takuya Hara, Tokyo (JP)

(73) Assignee: KOWA COMPANY, LTD., Aichi (JP)

(*) Notice: Subject to any disclaimer, the term of this patent is extended or adjusted under 35 U.S.C. 154(b) by 266 days.

(21) Appl. No.: 16/210,038

(22) Filed: Dec. 5, 2018

(65) Prior Publication Data

US 2019/0117059 A1 Apr. 25, 2019

Related U.S. Application Data

(63) Continuation of application No. 15/117,574, filed as application No. PCT/JP2015/053482 on Feb. 9, 2015, now abandoned.

(30) Foreign Application Priority Data

Feb. 12, 2014 (JP) ................................. 2014-024284

(51) Int. Cl.
*A61B 3/00* (2006.01)
*A61B 3/024* (2006.01)

(52) U.S. Cl.
CPC ............ *A61B 3/024* (2013.01); *A61B 3/0025* (2013.01); *A61B 3/0033* (2013.01); *A61B 3/0041* (2013.01); *A61B 3/0058* (2013.01)

(58) Field of Classification Search
CPC ............................... A61B 3/024; A61B 3/0025
USPC ....................................................... 351/224
See application file for complete search history.

(56) References Cited

U.S. PATENT DOCUMENTS

| 7,325,925 B1* | 2/2008 | Shimada ................ A61B 3/024 |
| | | 351/206 |
| 8,157,379 B2 | 4/2012 | Hara |
| 8,727,535 B2 | 5/2014 | Hara |
| 9,161,685 B2 | 10/2015 | Shimada |
| 9,826,897 B2 | 11/2017 | Shimada et al. |

FOREIGN PATENT DOCUMENTS

| JP | H06-054804 | 3/1994 |
| JP | 2007-195787 | 8/2007 |
| JP | 2011-206105 | 10/2011 |
| JP | 2013-132502 | 7/2013 |

OTHER PUBLICATIONS

International Search Report, corresponding to PCT/JP2015/053482, dated Apr. 21, 2015.

* cited by examiner

*Primary Examiner* — James C. Jones
(74) *Attorney, Agent, or Firm* — Duane Morris LLP

(57) ABSTRACT

In a perimetry to be conducted, designating an inspection region through a region designator, a perimeter is configured to set a required time of the perimetry (upper limit time) through an upper limit condition setter and to determine total number or positions of stimulus presentation spots based upon the upper limit time. In such a configuration, an examinee knows the time to finish the inspection, and is able to highly keep his (her) concentration in comparison with a case where the required time is not known, thereby improving precision of the inspection.

12 Claims, 7 Drawing Sheets

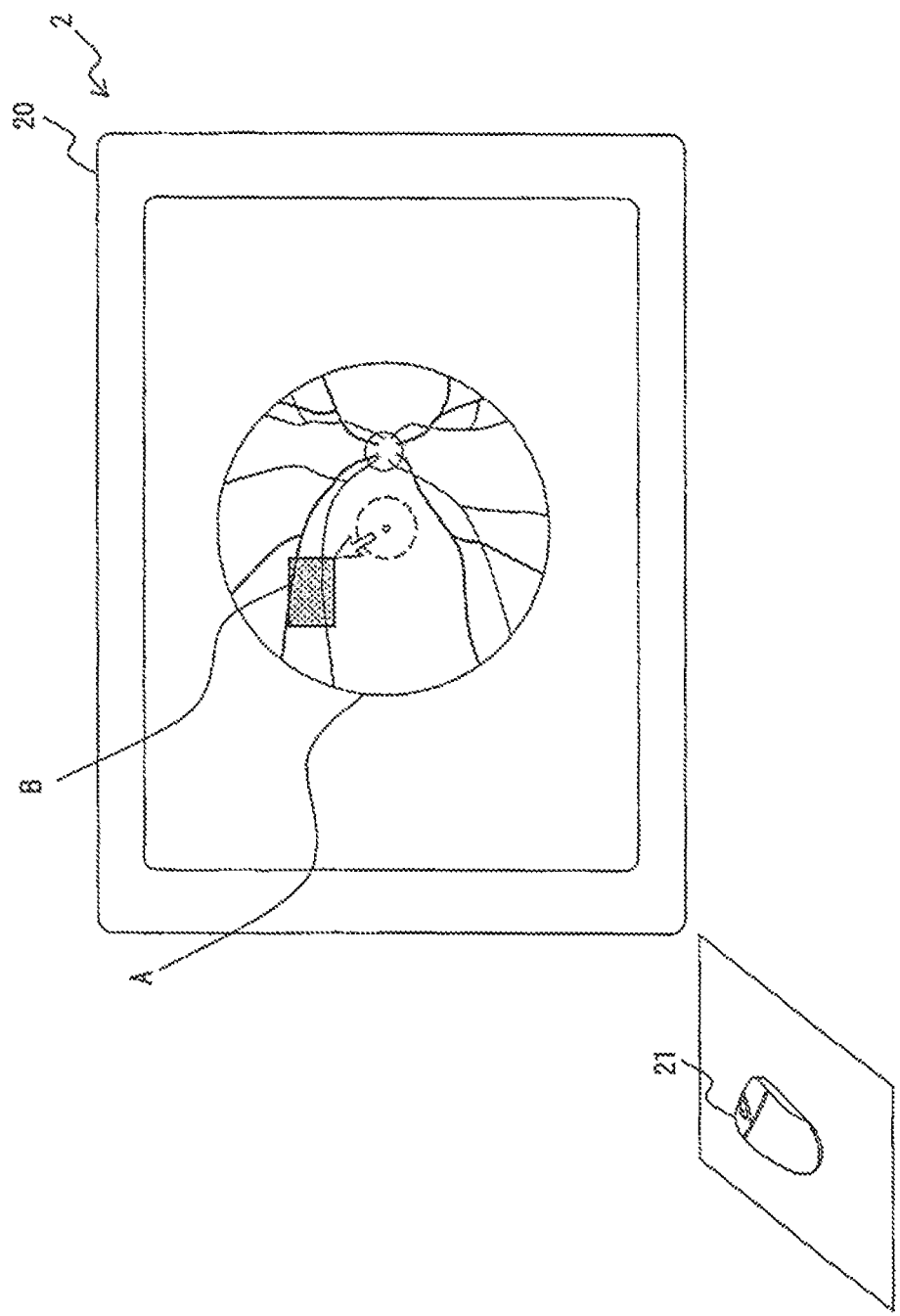

PERIMETER

CROSS-REFERENCE TO RELATED APPLICATION

This application is a continuation of co-pending U.S. patent application Ser. No.: 15/177,574, filed Aug. 9, 2016, which is a § 371 National Stage Entry of International Application Serial No. PCT/JP2015/053482, filed Feb. 9, 2015, which claims priority to Japanese patent Application No.: 2014-024284, filed on Feb. 12, 2014.

TECHNICAL FIELD

The invention relates to a perimeter for inspecting a visual field of an examinee in a state that the examinee fixates a predetermined stimulus, and especially to the perimeter that is configured to designate a region that is expected to be inspected.

BACKGROUND ART

The perimeter has been used in order to find ocular diseases, such as the glaucoma. A conventional problem in such a perimeter is that it takes a longer time to conduct a perimetry on the whole visual field that results in heavy burden on a patient.

Then, such a perimeter that the region on which the perimetry is conducted is designated on a fundus image, and the perimetry is conducted on such a designated region has been proposed (see Patent-related documents 1 and 2, for instance).

FIG.7 is a typical view that shows an example of a way of designating the region, a reference number A denotes the fundus image, and B denotes the designated region.

According to such a perimeter, it is possible to designate only the region on which the perimetry is to be conducted and conduct the perimetry on only such a region, and to shorten the perimetry time and reduce the burden on examinees and examiners, and to effectively detect the disorder of the visual field in comparison with a case where the perimetry is conducted on the whole visual field.

SUMMARY

The examinee is forced to fixate the fixation point and keep his (her) concentration till finish of the perimetry that results in rather heavy burden on the examinee although the perimetry time is shorter than the perimetry on the whole visual field. A lesion can be found with a high possibility in such an perimetry (that is, the perimetry which is conducted on the designated region), for this reason the perimetry with high precision is expected, and it is preferable to reduce the burden on the examinee as much as possible and keep the examinee's concentration.

An object of the invention is to provide the perimeter for solving the above-mentioned problems.

A first aspect of the invention is a perimeter (1) exemplarily shown in FIG. 1 for inspecting a visual field of an examinee in such a state the examinee fixates a fixation point, comprising: when a region on which a perimetry is expected (See B of FIG.2, and B1 to B3 of FIG. 3(a) to (c) and FIG. 4) is referred to as "the inspection region", an upper limit time for conducting the perimetry (Tmax) is referred to as "the upper limit time", a region to which stimuli are presented (see E1 to E3 of FIG. 3(a) to (c)) to is referred to as "the stimulus presentation region", and a spot to which the stimuli are presented (see $P_1$ of FIG. 4) in the stimulus presentation region is referred to as "the stimulus presentation spot";

a region designator (2) that is configured to display an image that shows a past perimetry result or a fundus image (both images are collectively referred to as "the designation images" hereinafter, see FIG. 2 and FIG. 3(a) to (c) and A of FIG. 4), and to designate the inspection region on the designation image (A);

a region determiner (3) that determines the stimulus presentation region (E1 to E3) based upon the designated inspection region (B, B1 to B3);

an upper limit condition setter (4) that sets total number of the stimulus presentation spots ($P_1$, . . . ) in the stimulus presentation region or the upper limit time (Tmax) (that are collectively referred to as "the upper limit condition" hereinafter);

a position determiner (5) that determines a position of each stimulus presentation spot so as to finish the perimetry under a condition lower than the upper limit condition (Tmax);

a stimulus presenter (6) that presents the stimulus with a predetermined brightness to each position determined through the position determiner (5) in order;

an operation device (7) to be operated by the examinee who perceived the presented stimulus; and a result judger (8) that judges the perimetry result based upon signals from the stimulus Presenter (6) and the operation device (7).

A second aspect of the invention is a perimeter (1) wherein the stimulus presenter (6) is configured to present the stimuli to each stimulus presentation spot, gradually changing their brightness twice or more, and the position determiner (5) determines the total number of the stimulus presentation spots and the positions when the upper limit time (Tmax) is set through the upper limit condition setter (4), and the position of each stimulus presentation spot when the total number of the stimulus presentation spots is set through the upper limit condition setter (4).

A third aspect of the invention is a perimeter (1), wherein the region determiner (3) determines the inspection region (B1) as the stimulus presentation region (E1) when a ratio that the inspection region occupies the designation image (A) with respect to an area or a length ("the occupancy ratio" hereinafter) is a predetermined standard value or higher (see FIG. 3(a), "the first state" hereinafter), and determines both regions (C2 and B2), the region separated in an up/down direction, an oblique direction and a right/left direction from the inspection region (B2) (see FIG. 3(b), "the spaced region" hereinafter) and the inspection region (B2) as the stimulus presentation region (E2) when the occupancy ratio is lower than a predetermined standard value (see FIG. 3(b), "the second state" hereinafter); and the stimulus presenter (6) is configured to present the stimuli in the inspection region (B1) in a case of the first state, and to present the stimuli in both regions (C2 and B2), the spaced region and the inspection region in a case of the second state.

A fourth aspect of the invention is the perimeter (1), wherein the position determiner (5) determines the stimulus presentation spots ($P_1$, . . . , $P_1'$, . . . ) such that "the total number of the stimulus presentation spots ($P_1$, . . . ) in the inspection region (B2 of FIG. 4)" is more than "the total number of the stimulus presentation spots ($P_1'$, . . . ) in the spaced region (C2)" in a case of the second state.

A fifth aspect of the invention is the perimeter (1), wherein the region designator (2) is configured to display the perimetry result image and to designate the inspection region (B, B1 to B3) on the perimetry result image, and the position determiner (5) is configured to determine at least one of the stimulus presentation spots in the past perimetry as the stimulus presentation spot at this time of the perimetry.

A sixth aspect of the invention is the perimeter (1), further comprising a state confirmor (9) that confirms a progress state of the perimetry during the perimetry based upon signals from the stimulus presenter (6) and the operation device (7), a finish time predictor (10) that predicts whether the perimetry finishes for all the stimulus presentation spots within the upper limit time (Tmax) based upon the progress state confirmed by the state confirmor (9), and a stimulus controller (11) that controls the stimulus presenter (6) not to present the stimuli to a part of the stimulus presentation spots if the finish time predictor (10) predicted that the perimetry does not finish on all the stimuli presentation spots within the upper limit time (Tmax).

A seventh aspect of the invention is the perimeter (1), wherein the position determiner (5) is configured to give a priority to each stimulus presentation spot, and the stimulus controller (11) is configured to omit the stimulus presentation to the spot having a lower priority.

A eighth aspect of the invention is the perimeter (1), further comprising a state confirmor (9) that confirms the progress state of the perimetry during the perimetry based upon the signals from the stimulus presenter (6) and the operation device (7), a finish time predictor (10) that predicts whether the perimetry finishes within the upper limit time (Tmax) for all stimulus presentation spots based upon the progress state confirmed by the state confirmor (9) and a stimulus controller (11) that controls the stimulus presenter (6) not to present the stimuli onto a part of the stimulus presentation spots if the finish time predictor (10) predicted that the perimetry does not finish within the upper limit time (Tmax) for all the stimulus presentation spots, wherein the region determiner (3) determines the inspection region (E1) as the stimulus presentation region (B1) when the ratio that the inspection region occupies the designation image (A) regarding the area and length ("the occupancy ratio" hereinafter) is a predetermined standard value or higher (see FIG. 3(a), "the first state" hereinafter), and determines both regions (C2 and B2), the regions separated in an up/down direction, an oblique direction and a right/left direction from the inspection region (B2) ("the spaced region" hereinafter), and the inspection region as the stimulus presentation region (E2) when the occupancy ratio is lower than a predetermined standard value (see FIG. 3(b), "the second state" hereinafter);

the stimulus presenter (6) presents the stimuli in the inspection region (B1) in a case of the first state, and presents the stimuli in both regions (C2 and B2), the spaced region (c2) and the inspection region (B2) in a case of the second state; and the stimulus controller (11) controls the stimulus presenter (6) not to present the stimulus onto a part of the stimulus presentation spots in the spaced region (C2) if the finish time predictor (10) predicted that the perimetry does not finish within the upper limit time (Tmax) for all the stimulus presentation spots and it is in the second state.

The number in parentheses shows the corresponding element in the drawings for the sake of convenience, accordingly, the descriptions are not restricted and bound by the descriptions on the drawings.

According to the $1^{st}$ and $2^{nd}$ aspects of the invention, the perimetry is configured to be conducted by setting the upper limit condition, so that the examinee knows a time to finish of the perimetry and is capable to keeping his (her) concentration in a case where the required time is not known. At the result, the precision of the perimetry can be improved.

According to the 3rd aspect of the invention, it is difficult for the examinee to predict the stimulus presentation spot even if the inspection region is narrow, thereby obtaining the correct perimetry result that does not receive the examinee's prediction.

According to the 4th aspect of the invention, the inspection region can be inspected within the determined upper limit condition in detail and the perimetry result with higher precision can be obtained.

According to the 5th aspect of the invention, it is possible to compare the past perimetry result and this time of the perimetry result with each other at the same stimulus presentation spot, and to grasp the progress state of the ocular diseases.

According to the 6th and 7th aspects of the invention, even if it takes a longer time for the perimetry on each presentation spot, it is possible to finish the perimetry within the upper limit time by omitting a part of the stimulus presentation.

According to the 8th aspect of the invention, it is possible to keep the perimetry precision of the inspection region in an excellent condition with no omission of stimulus presentation in the inspection region.

BRIEF DESCRIPTION OF DRAWINGS

FIG. 2 is a typical view that shows an example of a structure of a region designator.

FIG. 3A, FIG. 3B, and FIG. 3C are typical views exemplarily show positions of an inspection region and the like.

DETAILED DESCRIPTION

Embodiments of the invention are now explained, referring to appended FIGS. 1 through 6.

Figure 1:
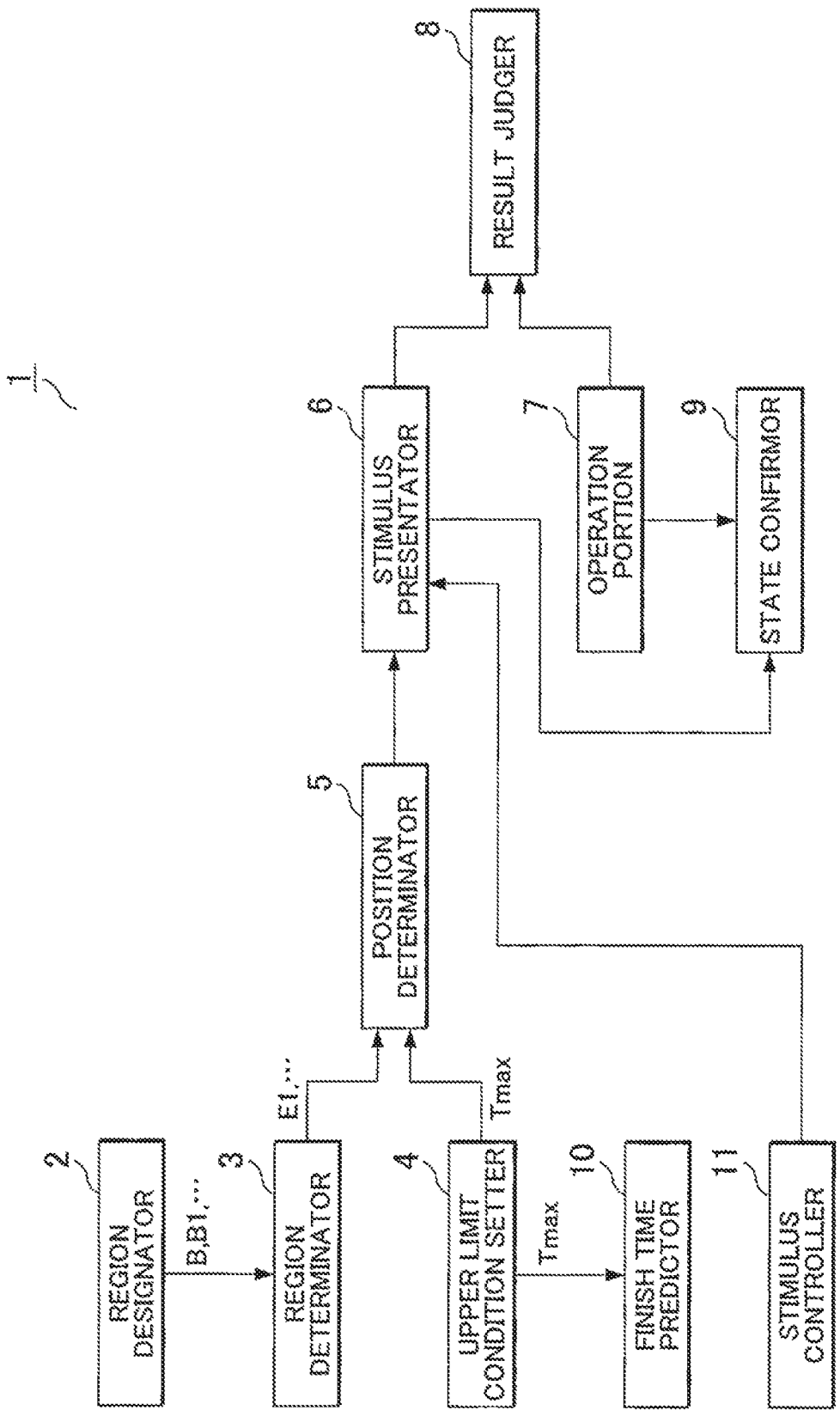
FIG. 1 is a block diagram that shows an example of a structure of a perimeter according to the present invention.
Figure 6:
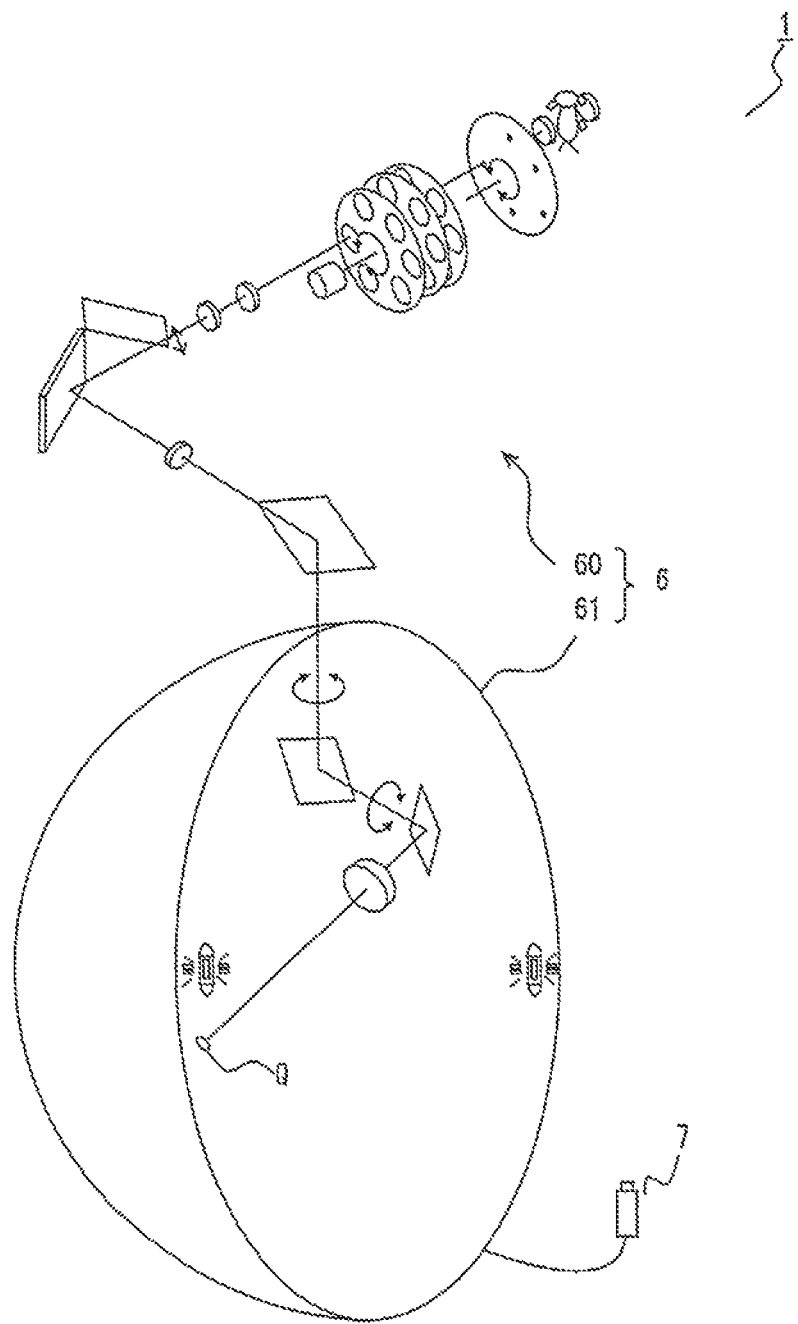
FIG. 6 is a perspective view that shows an example of a structure of the perimeter.
Figure 7:
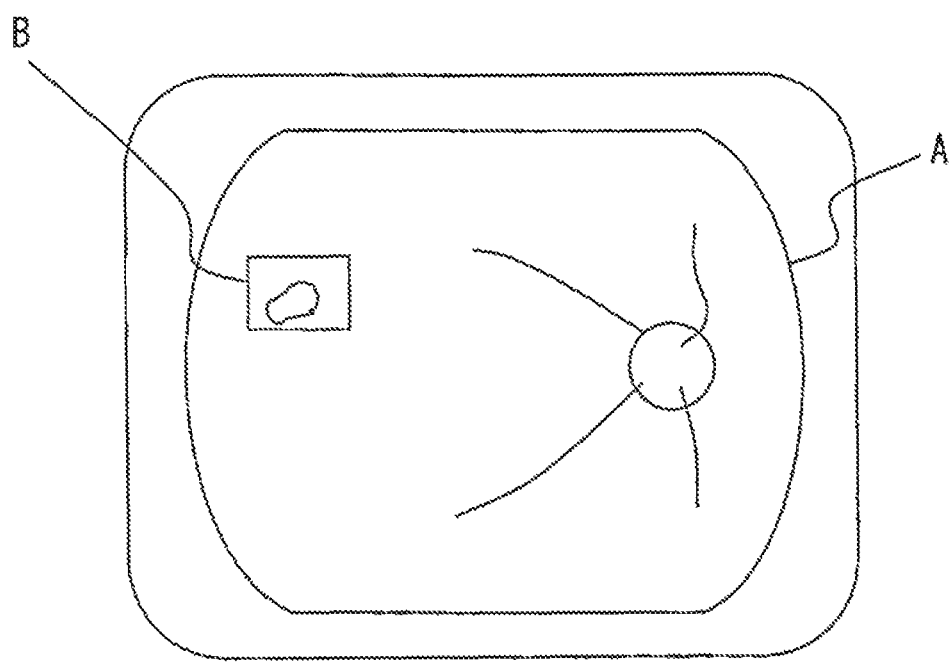
FIG. 7 is a typical view that schematically shows an example of a way of designating a region (inspection region) (conventional example).

A perimeter according to the invention that exemplarily shown with a reference number 1 of FIG. 1, is for testing a visual field of an examinee in a state that he (or she) fixates a predetermined fixation point, such as a central position of a visual field dome 61 exemplarily shown in FIG. 6), and has a region designator 2, a region determiner 3, an upper limit condition setter 4, a position determiner 5, a stimulus presenter 6, an operation device 7 and a result judger 8. The region designator 2 displays "an image that shows a result of a past perimetry ("the perimetry result image" hereinafter)" or "a normal fundus image that does not show the result of the perimetry (see a reference number A of FIG. 2, FIG. 3(a) to (c) and FIG. 4). The perimetry result image and the fundus image are referred to as "the designation image" hereinafter.), and designates a region on which the perimetry is to be done (see a reference number B of FIG. 2 and reference numbers B1 to B3 of FIG. 3(a) to (c) and FIG. 4. "the inspection region" hereinafter) on the designation image A. The region determiner 3 determines the region on which a stimulus is actually presented (see reference numbers E1 to E3 of FIG. 3(a) to (c). "the stimulus presentation region" hereinafter) based upon the designated inspection regions B, B1 to B3. The upper limit condition setter 4 sets "upper limit for conducting the perimetry ("the upper limit time" hereinafter) Tmax" or "total number of spots in the stimulus presentation region where the stimuli are presented ("the stimulus presentation spot" hereinafter) (both upper limit time and the total number are referred to as "the upper limit condition" hereinafter). The position determiner 5 determines a position of each stimulus presentation spot at least in order to finish the perimetry on a condition lower than the upper limit condition (that is, the time shorter than the upper limit time or the stimulus presentation spots the number of which is smaller than the total number). The stimulus presenter 6 presents the stimuli having a predetermined brightness in order at each position that is determined through the position determiner 5. The operation device 7 is operated by the examinee who perceives the presented stimulus. The result judger 8 judges the perimetry result based upon signals from the stimulus presenter 6 and the operation device 7.

If it is necessary to distinguish the inspection regions by their shapes and positions, reference numbers "B1, "B2" and "B3" are used, and when such a distinction is not necessary, only the reference number "B" is used in the following explanation. This is similar regarding the stimulus presentation region, and if it is necessary to distinguish the stimulus presentation regions by their shapes and positions, reference numbers "E1, "E2" and "E3" are used, and when such a distinction is not necessary, only the reference number "E" is used. Furthermore, it is similar regarding a spaced region, and reference numbers "C2" and "C3" are used if it is not necessary to distinguish the stimulus presentation regions by their shapes and positions, and only the reference number "C" is used when such a distinction is not necessary.

The perimetry is done on the designated region as the present invention since ocular diseases, such as the glaucoma, exists in such a region with a higher possibility, so that it is necessary to enhance the precision of the perimetry in comparison with a normal perimetry (that is, the perimetry which is done on whole visual field with no region designation), and necessary to highly keep the examinee's concentration during the perimetry. According to the present invention, the perimetry is configured to be done by setting the upper limit condition (concretely speaking, the upper limit time Tmax and the total number of the stimulus presentation spots), the examinee knows a predetermined required time till the finish of the perimetry, and is able to highly keep his (or her) concentration in comparison with the case where required predetermined time is not known. At the result, it is improve the precision of the perimetry.

Subsequently, respective elements comprising the perimeter are now explained.

<Region Designator>

Preferably, the region designator 2 exemplarily shown in FIG. 2 has a monitor 20, such as a liquid crystal display, and a monitor drive portion (not shown) through which the fundus image A and the perimetry result image of the examinee (not shown) are displayed on the monitor 20, and an input portion 21 for designating the inspection region B on a screen of the monitor 20. The input portion 21 exemplarily shown in FIG. 2 is a mouse, but may be a stylus pen, or the other well-known input device. The inspection region B exemplarily shown in FIG. 2 is a rectangular shape, but may have the other shape, such as a circle or an optional shape.

<Region Determiner>

The region on which the perimetry is expected (the inspection region) varies among patients. For instance, rather wider region may be inspected for some patients (the examinees) (for instance, see B1 of FIG. 3(a)), and it may be sufficient to inspect only the extremely narrow region for the other patients (see B2 and B3 of FIG. 3(b), (c)). In the case where the stimuli are presented on only the narrow inspection region, the patient may predict the rough region where the stimuli are presented and it is not possible to obtain the correct perimetry result by the influence of his (her) prediction. Then, preferably, the region determiner 3 in the invention determines the inspection region B1 as the stimulus presentation region E1 when the ratio that the inspection region B1 occupies the designation image A (that is, in the area of the fundus) that is the ratio regarding its area and length and is referred to as "occupancy ratio" hereinafter is a predetermined standard value or higher ("the first state" hereinafter) as exemplarily shown in FIG. 3(a), and determines both regions, the regions separated in an up/down direction, an oblique direction and a right/left direction from the inspection regions B2 and B3 ("the spaced regions" hereinafter), and the inspection regions B2 and B3 as the stimulus presentation regions E2 and E3 when the occupancy ratio is lower than a predetermined standard value as exemplarily shown in FIG. 3(b) and (c). Preferably, the stimulus presenter 6 presents the stimuli on the inspection region B in the case of the first state, and on both the spaced region C and the inspection region B in the case of the second state. In this case, "a predetermined value" is 60%, 70% or so of the designation image A (that is, the area of the ocular fundus) in the area or the maximum length (that is, the diameter of the designation image A that is almost a circle), and is the value with which the precision of the perimetry is expected to be similar to the case where the perimetry is conducted while the stimuli are presented to the whole visual field. In the case of the first state (that is, the case where the occupancy ratio is a predetermined standard value or higher), the examinee is difficult to predict the stimulus presentation spot since the inspection region itself is sufficiently wide, thereby obtaining the correct perimetry result that does not receive the influence of the examinee's prediction. In a case of the second state (that is, the occupation ratio is lower than a predetermined standard value), the stimuli are presented also to the spot spaced from the inspection region B (that is, the spaced region C) in addition to the inspection region B, so that the examinee is difficult to predict the stimulus presentation spot, thereby obtaining the correct result that does not receive the influence of the examinee's prediction. In the case of the second state, the stimuli are presented to both the inspection region B and the spaced region C under the condition lower than the upper limit condition. The spaced regions C is only one or more. The region determiner 3 may compare one of the area and the length of the inspection region with a predetermined standard value. Alternatively, the region determiner 3 may judge whether "the area" of the inspection region is a predetermined standard value or higher, or lower in a case where the dimension ratio of the length and the width of the inspection region is close to 1 (one) (that is, the dimensions of the length and width are almost equal), and may judge whether "the maximum length"is a predetermined standard value or higher, or lower in a case where the dimension ratio of the length and the width of the inspection region is extremely different.

Preferably, the position determiner 5 determines the stimulus presentation spots so that "the total number of the stimulus presentation spots ($P_1, \ldots$) in the inspection region (see B2 of FIG. 4)" are more than "the total number of the stimulus presentation spots ($P_1', \ldots$) in the spaced region (C2)" in the case of the second state. In a case where the total number of the stimulus presentation spots is 100 spots, for instance, the total number of the stimulus presentation spots in the inspection region B may be 70 spots and the total number of the stimulus presentation spots in the spaced region C may be 30 spots. In such a case, it is possible to inspect the inspection region B within the determined upper limit condition, such as the upper limit time Tmax), and to obtain the perimetry result with high precision.

Preferably, the space region C2 is set at the position symmetric with the inspection region B in the up/down direction on the basis of a horizontal base line HL (the horizontal line including a center of a retina G (that is, a center of a fovea) in the designation image A) in a case where it is in the second state and the inspection region B2 is on the position spaced from the horizontal base line HL. In such a case also, "the total number of the stimulus presentation spots in the inspection region B2" may be more than "the total number of the stimulus presentation spots in the spaced region C2". If the stimulus presentation spots ($P_1, \ldots$) in the inspection region B2 is referred to as "a main stimulus presentation spot", and the stimulus presentation spots ($P_1', \ldots$) in the spaced region C2 is referred to as "a sub stimulus presentation spot", one main stimulus presentation spot ($P_1$, for instance) may always be set at the position symmetric with the position of the sub stimulus presentation spot (for instance, $P_1'$) with respect to the horizontal base line HL. Besides, "the stimulus presented to the main stimulus presentation spot" and "the stimulus presented to the sub presentation spot" may have the same size and brightness. When comparing the perimetry results of the main stimulus presentation spot $P_1, \ldots$ and the sub stimulus presentation spot $P_1', \ldots$ that are symmetric in the up/down direction with each other in the above-mentioned case, the gap of the symmetry in the up/down direction can be found, thereby easily finding ocular diseases, such as the glaucoma.

Figure 3A:
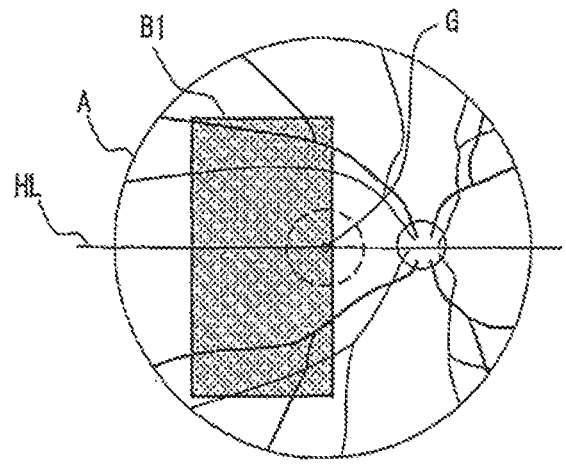
Figure 3B:
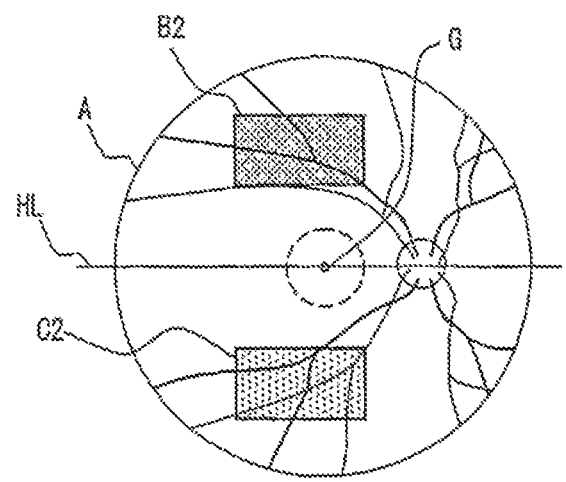
Figure 3C:
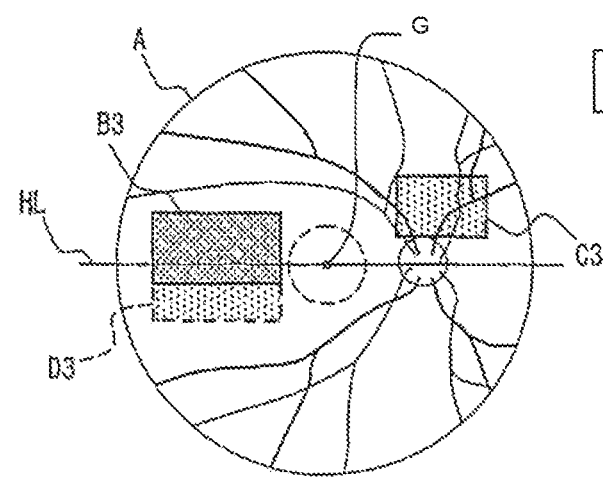
Figure 4:
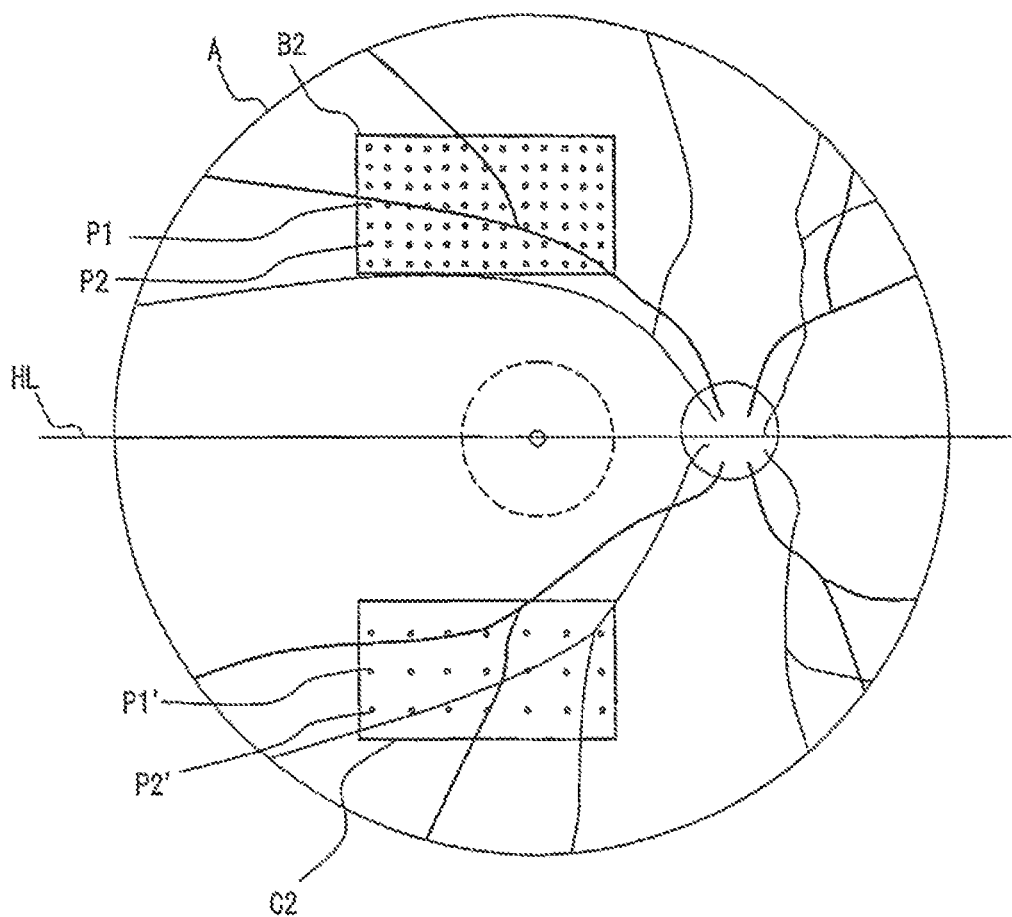
FIG. 4 is a typical view that shows an example of stimulus presentation spots in the inspection region and a spaced region.

On the contrary, in a case where it is in the second state, and the inspection region B3 includes the horizontal base line HL or approaches the horizontal base line HL, so that the region symmetric with the inspection region B3 on the basis of the horizontal base line HL ("the symmetric region" hereinafter) is not spaced from the inspection region B3 as exemplarily shown in FIG. 3(c), the spaced region (see C3) may be set at the position excluding one symmetric with respect to the horizontal base line HL (the position apart in the up/down direction, the lateral direction or the oblique direction). In such a case, the inspection region B3 and the spaced region C3 may be the stimulus presentation regions, or the inspection region B3, the spaced region C3 and the symmetric region D3 may be the stimulus presentation regions. In the latter case (that is, in the case where the inspection region B3, the spaced region C3 and the symmetric region D3 are the stimulus presentation regions and the stimulus presentation spot in the inspection region B3 is referred to as "the main presentation spot" and the stimulus presentation spot in the symmetric region D3 is referred to as "the sub stimulus presentation spot", one main stimulus presentation spot may always be set at the position symmetric with the position of the sub stimulus presentation spot on the basis of the horizontal base line HL. Besides, "the stimulus presented to the main stimulus presentation spot" and "the stimulus presented to the sub presentation spot" may have the same size and brightness. In such a case, it is difficult for the examinee to predict the stimulus presentation spot by presenting the stimuli on the space region C3, thereby obtaining the correct perimetry result that does not receive the influence of the examinee's prediction. At the same time, when comparing the perimetry results of the main stimulus presentation spot and the sub stimulus presentation spot that are symmetric in the up/down direction with each other, the gap of the symmetry in the up/down direction can be found, thereby easily finding ocular diseases, such as the glaucoma. In this case, the stimuli may be presented in such a state that "the total number of the stimulus presentation spots in the inspection region B3">"the total number of the stimulus presentation spots in the symmetric region D3">"the total number of the stimulus presentation spots in the spaced region C3". Besides, the stimuli may be presented in such a state that stimulus presentation density in the inspection region B3">"the stimulus presentation density in the symmetric region D3 (if the inspection region B3 overlaps the symmetric region D3 as exemplarily shown in FIG. 3(c), the spot that does not overlap the inspection region B3 in the symmetric region D3)>"the stimulus presentation density in the spaced region C3".

<Upper Limit Condition Setter>

There are various kinds of the upper limit condition setter 4, and these are a graphical user interface on the screen (and a pointing device for setting the upper limit condition on the interface), and some kind of switch attached to the perimeter, such as a dial switch, for instance. Such an upper limit condition setter 4 sets any one of "the upper limit time Tmax" and "the total number of the stimulus presentation spots". Concretely speaking, it has a function to set only the upper limit time Tmax, a function to set only the total number of the stimulus presentation spots, and a function to set both "the upper limit time Tmax" and "the total number of the stimulus presentation spots, and the examiner is able to select it as needed.

<Position Determiner>

Figure 5:
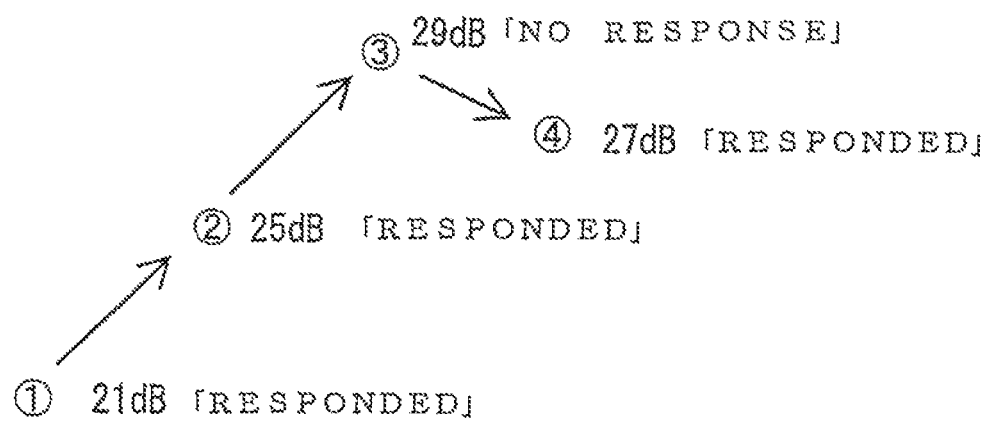
FIG. 5 is a conceptual view that shows a way of a threshold perimetry in one stimulus presentation spot.

Preferably, the position determiner 5 determines the total number N of the stimulus presentation spots and the positions in the stimulus presentation region E when the upper limit condition setter 4 sets the upper limit time Tmax, and determines the position of each stimulus presentation spot when the upper limit condition setter 4 sets the total number of the stimulus presentation spots. And, the stimulus presenter 6 presents the stimuli two times or more, gradually changing the brightness of the stimulus at each stimulus presentation spot (the details are mentioned hereinafter), and the position determiner 5 may determine the number of times to present the stimuli at each stimulus presentation spot (that is, the number of times to present the stimuli at each presentation spot, gradually changing the brightness, four times in the example as shown in FIG. 5 (1) to (4)). If the upper limit time that is set is Tmax and approximate time necessary for the perimetry for one stimulus presentation spot is t, the total number N of the stimulus presentation spots is obtained with Tmax÷t. As mentioned before, the stimulus presenter 6 sometimes presents the stimuli onto the spaced region C and the symmetric region D in addition to the inspection region B, and it is necessary for the position determiner 5 to determine the number $N_1$ of the stimulus presentation spots in the inspection region B, the number $N_2$ of the stimulus presentation spots in the spaced region C and the number $N_3$ of the stimulus presentation spots in the symmetric region D so as to be $N_1+N_2+N_3 \leq N$.

<Stimulus Presenter>

On the other hand, when the region designator 2 is configured to display the perimetry result image and designate the inspection region based upon the perimetry result image, the position determiner 5 may determine at least one of "the stimulus presentation spots in the past perimetry (the positions onto which the stimuli were presented) as "the stimulus presentation spots in this time of the perimetry (the positions onto which the stimuli to be presented). By doing so, the result of the past perimetry and the result of this time of the perimetry can be compared with each other in the same stimulus presentation spot, thereby grasping the progress of the ocular disease. Preferably, the perimetry images are stored, adding identification information of the patients, thereby comparing the perimetry results as mentioned before through the identification information. Preferably, the region designator 2 displays the perimetry result image, highlighting the spots which perimetry result was bad (the bad spots rather than a predetermined standard) that are the stimulus presentation spots in the past perimetry (the positions onto which the stimuli were actually presented). By doing so, it is easily grasp the regions to be inspected again. Furthermore, the position determiner 5 may determine "the spots which perimetry result was bad in the stimulus presentation spots in the past perimetry (the spots on which the stimuli were presented)" as "the stimulus presentation spots in this time of the perimetry (the spots on which the stimuli are to be presented)".

<Stimulus Presenter>

The stimulus presenter 6 is configured to present the stimuli, gradually changing their brightness at the respective stimulus presentation spots twice or more and to conduct a so-called threshold perimetry. FIG. 5 is a conceptual diagram that shows a way of the threshold perimetry at one stimulus presentation spot. In the instance as shown in FIG. 5, the stimuli are presented four times in order of (1)→(2)→(3)→(4), and the brightness of the respective stimuli are gradually changed in order of 21 dB→25 dB(rather darker than 21 dB)→29 dB (rather darker than 25 dB)→27 dB (rather brighter than 29 dB). Responses through the operation device 7 from the examinee are respectively "responded", "responded", "no response" "responded" in the stimulus presentation (1), (2), (3) and (4). In such a case, the result judger 8 judges the sensitivity of the retina in this spot (the stimulus presentation spot) is 27 dB.

As exemplarily shown in FIG. 6, the stimulus presenter 6 may be configured to have a projection optical system 60 for projecting the stimuli Q and the visual field dome (projection member) 61, but is not limited to such a configuration shown in FIG. 6. Any configuration may be taken as long as the stimuli are presented in the visual field of the examinee. For instance, two or more LED may be located and are selectively lighted. The projection member 61 as shown in FIG. 6 is in the shape of a hemisphere dome (visual field dome), but is not limited to such a configuration, and may have a curve surface excluding the hemispheric surface, or a flat surface.

When it is in the second state and the inspection region B and the spaced region C are not located on the positions symmetric in the up/down direction with respect to the horizontal base line HL, the stimulus presenter 6 may be configured to present the stimuli so as to make "the stimulus presented onto the spaced region C" bigger than and/or brighter than "the stimulus presented onto the spaced region C". By doing so, the examinee is easy to perceive the stimuli that are presented onto the spaced region C, it is possible to prevent the examinee's concentration from being poured onto only the inspection region B, and obtain the correct perimetry result that does not receive the influence of the examinee's prediction.

<Operation Device>

Preferably, a well-known mechanism, such as a push switch, is used for the above-mentioned operation device 7.

<The Other Elements>

The perimeter 1 according to the present invention presents the stimuli onto two or more spots in the stimulus presentation regions E1 to E3, and presents the stimuli twice or more, receiving the responses from the examinee, not once for one spot. If the response from the examinee is late, then, it takes a longer time for the perimetry, so that the perimetry may not finish within the upper limit time Tmax.

Preferably, the perimeter 1 according to the invention has a state confirmor 9, a finish time predictor 10 and a stimulus controller 11. The state confirmor 9 confirms the progress state of the perimetry during the perimetry based upon signals from the stimulus presenter 6 and the operation device 7. The finish time predictor 10 predicts whether the perimetry finishes within the upper limit time Tmax for all stimulus presentation spots based upon the progress state confirmed by the state confirmor 9. The stimulus controller 11 controls the stimulus presenter 6 not to present the stimulus onto a part of the stimulus presentation spots if the finish time predictor 10 predicted the perimetry does not finish within the upper limit time Tmax for all stimulus presentation spots. The perimetry in the present invention is conducted, receiving the responses from the examinee, and it may take a longer time for the perimetry on each stimulus presentation spot. However, it is possible to finish the perimetry within the upper limit time Tmax by omitting a part of the stimulus presentation when providing the state confirmor 9, the finish time predictor 10 and the stimulus controller 11. In such a case, the finish time predictor 10 may have a time measurer for measuring a passage time from the start of the perimetry. In this case, the stimulus presentation may be omitted in such a way that when the stimuli are presented to one stimulus presentation spot, gradually changing the brightness, the number of the stimulus presentation is reduced, or all stimulus presentation is omitted to some stimulus presentation spot (the spot to which the stimulus presentation is scheduled). When presenting the stimulus in the regions symmetric in the up/down direction in order to find the ocular disease, the latter method (that is, the method of omitting all stimulus presentation to some stimulus presentation spot) may be taken, not the former one.

Preferably, the above-mentioned "a part of stimulus presentation spots (that is, the spots that are omitted to be presented by the stimulus controller 11)" is not ones in the inspection region B, but ones in the spaced region C. When the finish time predictor 10 predicted the perimetry does not finish within the upper limit time Tmax for all the stimulus presentation spots and it is in the second state, the stimulus controller 11 may control the stimulus presenter 6 not to present the stimuli onto a part of the stimulus presentation spots in the spaced region C. By doing so, the stimulus presentation is not omitted on the inspection region B, thereby well keeping the precision of the perimetry in the inspection region B.

Preferably, the finish time predictor 10 obtains from respective data, the upper limit time Tmax that is set, already passed time $T_0$, number $N_a$ of the stimulus presentation spots on which stimulus presentation does not finish (the number obtained from the information from the state confirmor 9) and approximate time required for the perimetry on one stimulus presentation spot, the time left for the perimetry "Tmax-$T_0$" and time necessary for remaining perimetry "$N_a \times t$", and compares both times. Preferably, the above-mentioned time t (that is, the approximate time necessary for the perimetry on one stimulus presentation spot) is obtained from the respective data, "the number n of the stimulus presentation on each stimulus presentation spot (the number of times that is expected)", "the expected response time $\Delta t1$ of the examinee (the time from the presentation of the stimulus till the response from the examinee)" and "the time $\Delta t2$ till the next stimulus presentation if no response is received from the examinee (the time that is set). Preferably, the position determiner 5 is configured to give the respective stimulus presentation spots priority (the orders from the view of the importance of the perimetry), and the stimulus controller 11 omits the stimulus presentation on the spot having the lower priority (the stimulus presentation spot). Furthermore, if the perimetry is conducted earlier than expectation after omitting a part of the stimulus presentation and the finish time predictor 10 predicts the perimetry finishes within the above-mentioned upper limit time Tmax, the stimulus controller 11 may conduct the stimulus presentation that has been omitted at this time.

EXPLANATION OF REFERENCE NUMBERS

1 . . . perimeter
2 . . . region designator
3 . . . region determiner
4 . . . upper limit condition setter
5 . . . position determiner
6 . . . stimulus presenter
7 . . . operation device
8 . . . result judger
9 . . . state confirmor
10 . . . finish time predictor
11 . . . stimulus controller
A . . . fundus image
B, B1~B3 . . . inspection region
C2, C3 . . . spaced region
E1~E3 . . . stimulus presentation region
$P_1, \ldots, P_1', \ldots, \ldots$ stimulus presentation spot
Tmax . . . upper limit time

We claim:

1. A method for conducting a perimetry on an examinee that enables the examinee to better concentrate on the perimetry, the method comprising:
    displaying a designation image on a monitor, the designation image comprising an image that shows a past perimetry result image or a fundus image and has a center;
    designating a portion of the designation image as an inspection region, wherein the inspection region is a region on which the perimetry is to be performed;
    determining a first stimulus presentation region within the designation image based upon the designated inspection region,
        wherein,
        the first stimulus presentation region includes the designated inspection region,
        the first stimulus presentation region is a region in which one or more visual stimuli are presented to the examinee at corresponding stimuli presentation spots;
    setting an upper limit condition for the perimeter,
        wherein,
        the upper limit condition is either an upper limit time duration for conducting the perimetry or a total number of the stimuli presentation spots in the first stimulus presentation region to which the one or more visual stimuli are to be presented;
    determining a position of each of the spots in the first stimulus presentation region that enables completing the perimetry within the upper limit condition;
    presenting the one or more visual stimuli having a predetermined brightness to the corresponding spots in the first stimulus presentation region;
    wherein an occupancy ratio is defined as a ratio of the area of the inspection region to the area of the designation image;
    wherein when the occupancy ratio is less than a predetermined standard value, a second stimulus presentation region is defined at a position symmetric with the first stimulus presentation region with respect to a horizontal base line defined through the center of the designation image and the one or more visual stimuli are presented to the second stimulus presentation region in addition to the first stimulus presentation region, in order to prevent the examinee from predicting the location of the spots to which one or more visual stimuli are being presented.

2. The method of claim 1, wherein the predetermined standard value is 70%.

3. The method of claim 1, wherein the predetermined standard value is 60%.

4. The method of claim 1, wherein when the occupancy ratio is less than the predetermined value, the total number of the stimuli presentation spots in the first stimulus presentation region is greater than the total number of the stimuli presentation spots in the second stimulus presentation region.

5. The method of claim 1, wherein one of the stimuli presentation spots in the first stimulus presentation region is set at a position symmetric with the position of one the stimuli presentation spots in the second stimulus presentation region with respect to the horizontal base line.

6. The method of claim 5, wherein one of the stimuli presentation spots in the first stimulus presentation region has the same size and brightness as one of the stimuli presentation spots in the second stimulus presentation region.

7. The method of claim 1, wherein the second stimulus presentation region is spaced apart from the first stimulus presentation region.

8. The method of claim 1, wherein when the first stimulus presentation region is positioned on the horizontal base line so that the second stimulus presentation region is not spaced apart from the first stimulus presentation region, a third stimulus presentation region is defined at a location that is spaced apart from the first stimulus presentation region and the one or more visual stimuli are presented to the third stimulus presentation region in addition to the first stimulus presentation region and the second stimulus presentation region.

9. The method of claim 8, wherein when the occupancy ratio is less than the predetermined value, the total number of the stimuli presentation spots in the first stimulus presentation region is greater than the total number of the stimuli presentation spots in the second stimulus presentation region and the third stimulus presentation region.

10. The method of claim 1, further comprising:
displaying a past perimetry result image on the monitor and designating the inspection region on the past perimetry result image; and
determining at least one of the stimulus presentation spots in the past perimetry result image as the stimulus presentation spot for the perimetry.

11. The method of claim 1, further comprising:
predicting whether the perimetry finishes within the upper limit time duration for conducting the perimetry; and
if the perimetry is predicted to not finish within the upper limit time duration, omitting presentation of one or more visual stimuli to the stimulus presentation spots, in order to shorten the perimetry time duration.

12. The method of claim 11, further comprising:
predicting whether the perimetry finishes within the upper limit time duration for conducting the permetry; and
if the perimetry is predicted to not finish within the upper limit time duration, omitting presentation of one or more visual stimuli to the stimulus presentation spots in the second stimulus presentation region.

* * * * *